US012770741B2

(12) United States Patent
Sankaran et al.

(10) Patent No.: US 12,770,741 B2
(45) Date of Patent: Oct. 20, 2026

(54) SYSTEMS AND METHODS FOR IMAGE PROCESSING TO DETERMINE BLOOD FLOW

(71) Applicant: HeartFlow, Inc., Redwood City, CA (US)

(72) Inventors: Sethuraman Sankaran, Redwood City, CA (US); Leo J. Grady, Darien, CT (US); Charles A. Taylor, Redwood City, CA (US)

(73) Assignee: Heartflow, Inc., San Francisco, CA (US)

(*) Notice: Subject to any disclaimer, the term of this patent is extended or adjusted under 35 U.S.C. 154(b) by 1430 days.

(21) Appl. No.: 17/388,655

(22) Filed: Jul. 29, 2021

(65) Prior Publication Data

US 2021/0358635 A1 Nov. 18, 2021

Related U.S. Application Data

(63) Continuation of application No. 15/668,943, filed on Aug. 4, 2017, now Pat. No. 11,087,884, which is a continuation of application No. 14/974,158, filed on Dec. 18, 2015, now Pat. No. 9,805,168, which is a continuation of application No. 13/864,996, filed on Apr. 17, 2013, now Pat. No. 9,424,395.

(60) Provisional application No. 61/772,401, filed on Mar. 4, 2013.

(51) Int. Cl.

| | |
|---|---|
| ***G16H 50/50*** | (2018.01) |
| ***A61B 5/00*** | (2006.01) |
| ***A61B 5/02*** | (2006.01) |
| ***A61B 5/021*** | (2006.01) |
| ***A61B 5/026*** | (2006.01) |
| ***A61B 6/00*** | (2024.01) |
| ***A61B 6/03*** | (2006.01) |
| ***A61B 6/50*** | (2024.01) |
| ***G06T 7/00*** | (2017.01) |

(52) U.S. Cl.

CPC ......... *G16H 50/50* (2018.01); *A61B 5/02007* (2013.01); *A61B 5/02028* (2013.01); *A61B 5/026* (2013.01); *A61B 5/7278* (2013.01); *A61B 6/032* (2013.01); *A61B 6/504* (2013.01); *A61B 6/5217* (2013.01); *G06T 7/0012* (2013.01); *A61B 5/021* (2013.01); *G06T 2207/10081* (2013.01); *G06T 2207/30104* (2013.01)

(58) Field of Classification Search

None

See application file for complete search history.

(56) References Cited

U.S. PATENT DOCUMENTS

| | | | | |
|---|---|---|---|---|
| 7,912,528 | B2 * | 3/2011 | Krishnan ............... G16H 50/20 600/407 | |
| 8,315,812 | B2 | 11/2012 | Taylor | |
| 2010/0130878 | A1 | 5/2010 | Lasso | |
| 2011/0071404 | A1 | 3/2011 | Schmitt et al. | |
| 2012/0022844 | A1 | 1/2012 | Teixeira | |
| 2012/0041318 | A1 | 2/2012 | Taylor | |
| 2013/0028494 | A1 | 1/2013 | Groth et al. | |
| 2015/0278727 | A1 | 10/2015 | Sankaran et al. | |

FOREIGN PATENT DOCUMENTS

| | | | |
|---|---|---|---|
| CN | 102834847 | A | 12/2012 |
| JP | 2013534154 | A | 9/2013 |
| WO | 03030074 | A1 | 4/2003 |
| WO | WO 2011/128806 | | 10/2011 |
| WO | WO2012/021307 | | 2/2012 |
| WO | WO 2012/021307 | A2 | 2/2012 |
| WO | 2015024934 | A1 | 2/2015 |

OTHER PUBLICATIONS

Patil et al. (International Journal of Computer Science and Mobile Computing (2013) vol. 2:22-27).*

Hammer et al. (Ultrasound in Med and Biol (2009) vol. 35, No. 12:2069-2083).*

Grbic et al. (MICCAI 2013, Part II, LNCS 8150:395-402; K. Mori (Eds.) (2013), published Jan. 1, 2013, Springer-Verlag, Berlin Heidelberg).*

Antiga, Luca et al. "An image-based modeling framework for patient-specific computational hemodynamics." Medical & biological engineering & computing vol. 46,11 (2008): 1097-112. doi: 10.1007/s11517-008-0420-1.

De Santis, G., Mortier, P., De Beule, M. et al. Patient-specific computational fluid dynamics: structured mesh generation from coronary angiography. Med Biol Eng Comput 48, 371-380 (2010).

(Continued)

*Primary Examiner* — Lori A. Clow

(74) *Attorney, Agent, or Firm* — Bookoff McAndrews, PLLC

(57) ABSTRACT

Embodiments include systems and methods for determining cardiovascular information for a patient. A method includes receiving patient-specific data regarding a geometry of the patient's vasculature; creating an anatomic model representing at least a portion of the patient's vasculature based on the patient-specific data; and creating a computational model of a blood flow characteristic based on the anatomic model. The method also includes identifying one or more of an uncertain parameter, an uncertain clinical variable, and an uncertain geometry; modifying a probability model based on one or more of the identified uncertain parameter, uncertain clinical variable, or uncertain geometry; determining a blood flow characteristic within the patient's vasculature based on the anatomic model and the computational model of the blood flow characteristic of the patient's vasculature; and calculating, based on the probability model and the determined blood flow characteristic, a sensitivity of the determined fractional flow reserve to one or more of the identified uncertain parameter, uncertain clinical variable, or uncertain geometry.

15 Claims, 3 Drawing Sheets

(56) References Cited

OTHER PUBLICATIONS

Steinman, David A., Image-Based Computational Fluid Dynamics Modeling in Realistic Arterial Geometries. Annals of Biomedical Engineering 30, 483-497 (2002).

International Search Report issued in corresponding International PCT Application No. PCT/US2014/019001, mailed Jun. 3, 2014.

Sethuraman Sankaran; Alison L. Marsden; "A Stochastic Collocation Method for Uncertainty Quantification and Propagation in Cardiovascular Simulations" Journal of Biomechanical Engineering, Mar. 2011, ASME, pp. 1-12.

International Preliminary Report on Patentability mailed on Sep. 17, 2015, in corresponding International PCT Patent Application No. PCT/US2014/019001, filed on Feb. 27, 2014 (10 pages).

Patent Examination Report No. 1 mailed on Oct. 8, 2015, in corresponding Australian Patent Application No. 2014226326, filed on Feb. 27, 2014 (3 pages).

Communication pursuant to Article 94(3) EPC mailed on Jul. 22, 2015, in corresponding European Patent Application No. 14 713 283.1, filed on Aug. 4, 2014 (6 pages).

Communication pursuant to Article 94(3) EPC mailed on Feb. 5, 2016, in corresponding European Patent Application No. 14 713 283.1, filed on Aug. 4, 2014 (6 pages).

Liu, Meilin et al., "Adaptive sparse grid algorithms with applications to electron magnetic scattering under uncertainty", Applied Numerical Mathematics, 2011, 61, pp. 24-37.

HeartFlow FFRct Analysis Receives Regulatory Approval in Japan, Nov. 17, 2016, Business Wire (available at http://www.businesswire.com/news/home/20161117005294/en/HeartFlow-FFRct-Analysis-Receives-Regulatory-Approval-Japan). Last accessed Mar. 22, 2017. 2 pages.

*NICE Guidance Recommends HeartFlow FFRct Analysis to Help Determine Cause of Stable Chest Pain in Patients*, Feb. 13, 2017, YAHOO! Finance (available at http://finance.yahoo.com/news/nice-guidance-recommends-heartflow-ffrct-070000377.html). Last accessed Mar. 22, 2017. 4 pages.

Elnakib et al. (2011) Medical Image Segmentation: A Brief Survey (Chapter 1). In: El-Baz A., Acharya UR., Laine A., and Suri, J. (eds) Multi Modality State-of-the-Art Medical Image Segmentation and Registration Methodologies. Springer, New York, NY:1-40.

Deschamps et al. in International Congress Series (2004) vol. 1268:75-80.

* cited by examiner

SYSTEMS AND METHODS FOR IMAGE PROCESSING TO DETERMINE BLOOD FLOW

CROSS-REFERENCE TO RELATED APPLICATIONS

This application is a continuation of and claims the benefit of priority to U.S. Nonprovisional patent application Ser. No. 15/668,943, filed Aug. 4, 2017, which is a continuation of and claims the benefit of priority to U.S. Nonprovisional patent application Ser. No. 14/974,158 (now U.S. Pat. No. 9,805,168), filed Dec. 18, 2015, which is a continuation of and claims the benefit of priority to U.S. Nonprovisional patent application Ser. No. 13/864,996 (now U.S. Pat. No. 9,424,395), filed Apr. 17, 2013, which claims the benefit of priority from U.S. Provisional Patent Application No. 61/772,401, filed Mar. 4, 2013, the entireties of each of which are herein incorporated by reference.

TECHNICAL FIELD

Embodiments of the present disclosure relate to methods and systems for patient-specific modeling of blood flow and, more particularly, to methods and systems for sensitivity analysis in patient-specific modeling of blood flow.

BACKGROUND

Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A need exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it can neither be used to predict changes in coronary blood flow, pressure, or myocardial perfusion under other physiologic states (e.g., exercise), nor can it be used to predict outcomes of interventions.

Thus, patients may require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to a procedure referred to as an "oculostenotic reflex", in which interventional cardiologists insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of increased coronary blood flow, e.g., when induced by intravenous administration of adenosine. Blood pressures may be measured by inserting a pressure wire into the patient. Thus, the decision to treat a lesion based on the determined FFR may be made after the initial cost and risk of diagnostic cardiac catheterization has already been incurred.

To reduce the above disadvantages of invasive FFR measurements, HeartFlow Inc. has developed methods for assessing coronary anatomy, myocardial perfusion, and coronary artery flow noninvasively. Specifically, computational fluid dynamics (CFD) simulations have been successfully used to predict spatial and temporal variations of flow rate and pressure of blood in arteries, including FFR. Such methods and systems benefit cardiologists who diagnose and plan treatments for patients with suspected coronary artery disease, and predict coronary artery flow and myocardial perfusion under conditions that cannot be directly measured, e.g., exercise, and to predict outcomes of medical, interventional, and surgical treatments on coronary artery blood flow and myocardial perfusion.

However, computational modeling of hemodynamics involves reconstructed geometry of the patients' arteries, which is facilitated through high-resolution imaging. For example, many CFD frameworks for noninvasively calculating FFR assume that: (i) the geometry is known with certainty, (ii) clinical variables such as blood pressure, hematocrit, myocardial mass, etc. are known with certainty, and/or (iii) boundary conditions at the inlet and outlets of the computational model are known with certainty. However, in reality, the FFR predicted using CFD varies based on the accuracy of the available data and mathematical models that describe hemodynamics in the arteries. As a result, there is a need for methods and systems for incorporating and quantifying the effects of uncertainties in the available data, as well as mathematical models. In addition, there is a need for methods and systems for assigning confidence intervals to determined FFR values as well as rank the sensitivity of the FFR calculation to different parameters.

The foregoing general description and the following detailed description are exemplary and explanatory only and are not restrictive of the disclosure.

SUMMARY

In accordance with an embodiment, systems are disclosed for determining cardiovascular information for a patient. A system includes at least one computer system configured to: receive patient-specific data regarding geometry of at least the patient's coronary vasculature; create a three-dimensional model representing at least a portion of the patient's coronary vasculature based on the patient-specific data; and identify one or more of an uncertain parameter, an uncertain clinical variable, and an uncertain geometry. The computer system is also configured to modify a probability model based on one or more of the identified uncertain parameter, uncertain clinical variable, or uncertain geometry; determine a blood flow characteristic within the patient's coronary vasculature based on the three-dimensional model and a model of the blood flow characteristic of the patient's coronary vasculature; and calculate, based on the probability model and the determined blood flow characteristic, a sensitivity of the determined blood flow characteristic to one or more of the identified uncertain parameter, uncertain clinical variable, or uncertain geometry.

In accordance with another embodiment, methods are disclosed for determining cardiovascular information for a patient, using at least one computer system. One method includes: receiving patient-specific data regarding geometry of the patient's coronary vasculature; creating a three-dimensional model representing at least a portion of the patient's coronary vasculature based on the patient-specific data; and identifying one or more of an uncertain parameter, an uncertain clinical variable, and an uncertain geometry. The method also includes modifying a probability model based on one or more of the identified uncertain parameter, uncertain clinical variable, or uncertain geometry; determining a blood flow characteristic within the patient's coronary vasculature based on the three-dimensional model and a model of the blood flow characteristic of the patient's coronary vasculature; and calculating, based on the probability model and the determined blood flow characteristic, a sensitivity of the determined fractional flow reserve to one or more of the identified uncertain parameter, uncertain clinical variable, or uncertain geometry.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

DESCRIPTION OF THE EMBODIMENTS

Reference will now be made in detail to exemplary embodiments, examples of which are illustrated in the accompanying drawings. Wherever possible, the same reference numbers will be used throughout the drawings to refer to the same or like parts.

In an exemplary embodiment, a method and system determines information relating to blood flow in a specific patient using information retrieved from the patient noninvasively. Various embodiments of such a method and system are described in greater detail in U.S. Pat. No. 8,315,812, filed Jan. 25, 2011, and entitled "Method and System for Patient-Specific Modeling of Blood Flow," which is hereby incorporated by reference in its entirety.

In some embodiments, the information determined by the method and system may relate to blood flow in the patient's coronary vasculature. Alternatively, the determined information may relate to blood flow in other areas of the patient's vasculature, such as carotid, peripheral, abdominal, renal, and cerebral vasculature. The coronary vasculature includes a complex network of vessels ranging from large arteries to arterioles, capillaries, venules, veins, etc. The coronary vasculature circulates blood to and within the heart and includes an aorta that supplies blood to a plurality of main coronary arteries (e.g., the left anterior descending (LAD) artery, the left circumflex (LCX) artery, the right coronary (RCA) artery, etc.), which may further divide into branches of arteries or other types of vessels downstream from the aorta and the main coronary arteries. Thus, the exemplary method and system may determine information relating to blood flow within the aorta, the main coronary arteries, and/or other coronary arteries or vessels downstream from the main coronary arteries. Although the aorta and coronary arteries (and the branches that extend therefrom) are discussed below, the disclosed method and system may also apply to other types of vessels.

In an exemplary embodiment, the information determined by the disclosed methods and systems may include, but is not limited to, various blood flow characteristics or parameters, such as blood flow velocity, pressure (or a ratio thereof), flow rate, and FFR at various locations in the aorta, the main coronary arteries, and/or other coronary arteries or vessels downstream from the main coronary arteries. This information may be used to determine whether a lesion is functionally significant and/or whether to treat the lesion. This information may be determined using information obtained noninvasively from the patient. As a result, the decision whether to treat a lesion may be made without the cost and risk associated with invasive procedures.

Figure 1:
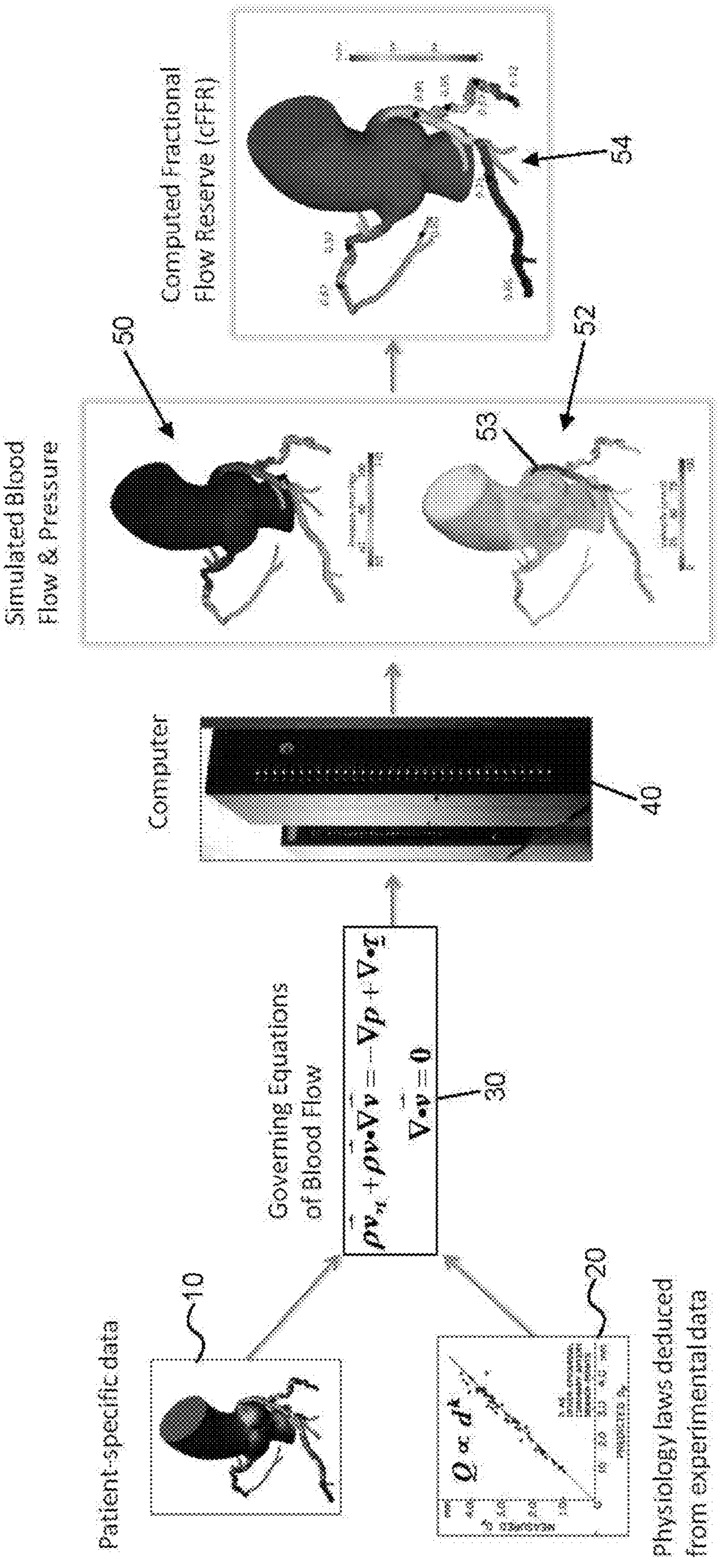
FIG. 1 is a schematic diagram of a system for providing various information relating to coronary blood flow in a specific patient, according to an exemplary embodiment.

FIG. 1 shows aspects of a system for providing information relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, a plurality of equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 can be solved to determine information (e.g., pressure, velocity, FFR, etc.) about the coronary blood flow in the patient's anatomy at various points in the anatomy represented by the model 10.

The equations 30 may be solved using a computer 40. Based on the solved equations, the computer 40 may output one or more images or simulations indicating information relating to the blood flow in the patient's anatomy represented by the model 10. For example, the image(s) may include a simulated blood pressure model 50, a simulated blood flow or velocity model 52, a computed FFR (cFFR) model 54, etc., as will be described in further detail below. The simulated blood pressure model 50, the simulated blood flow model 52, and the cFFR model 54 provide information regarding the respective pressure, velocity, and cFFR at various locations along three dimensions in the patient's anatomy represented by the model 10. cFFR may be calculated as the ratio of the blood pressure at a particular location in the model 10 divided by the blood pressure in the aorta, e.g., at the inflow boundary of the model 10, under conditions of increased coronary blood flow, e.g., conventionally induced by intravenous administration of adenosine.

In an exemplary embodiment, the computer 40 may include one or more non-transitory computer-readable storage devices that store instructions that, when executed by a processor, computer system, etc., may perform any of the actions described herein for providing various sources of information relating to blood flow in the patient. The computer 40 may include a desktop or portable computer, a workstation, a server, a personal digital assistant, or any other computer system. The computer 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer 40 to a network, a display adapter for connecting the computer 40 to a display, etc. For example, the display may be used to display the three-dimensional model 10 and/or any images generated by solving the equations 30, such as the simulated blood pressure model 50, the simulated blood flow model 52, and/or the cFFR model 54.

Figure 2:
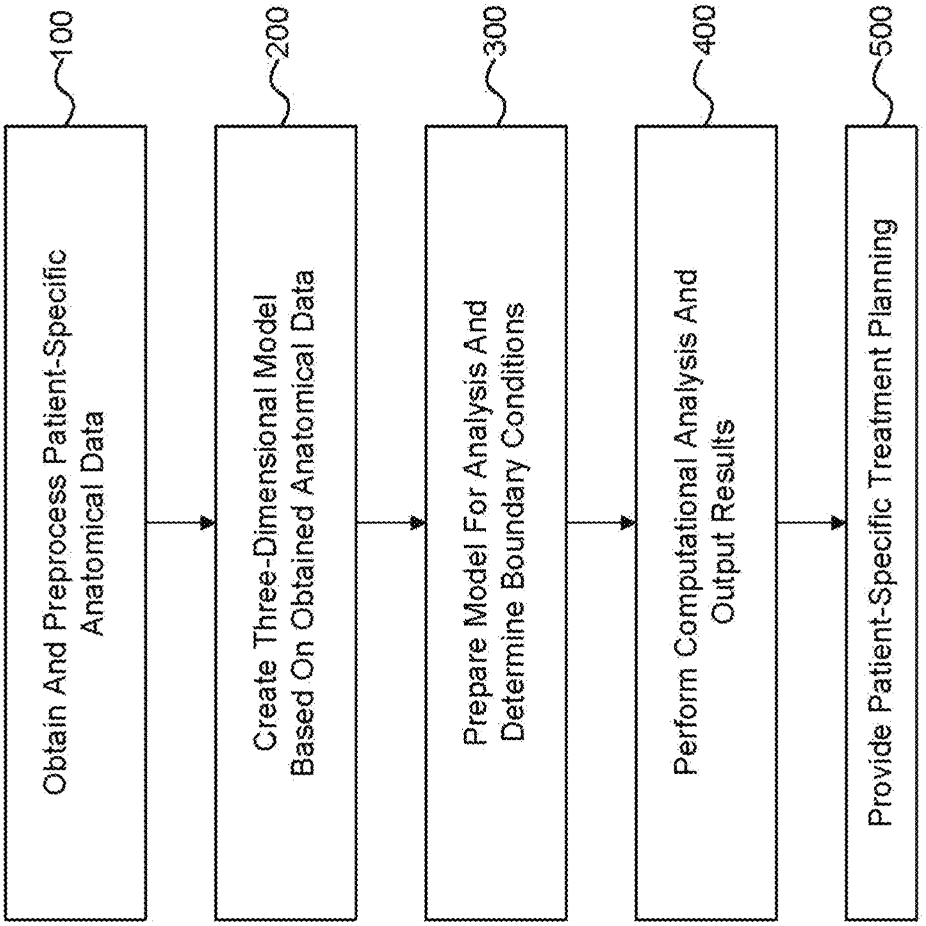
FIG. 2 is a flow chart of a method for providing various information relating to blood flow in a specific patient, according to an exemplary embodiment.

FIG. 2 shows aspects of a method for providing various sources of information relating to blood flow in a specific patient, according to another exemplary embodiment. The method may include obtaining patient-specific anatomical data, such as information regarding the patient's anatomy (e.g., at least a portion of the aorta and a proximal portion of the main coronary arteries (and the branches extending therefrom) connected to the aorta), and preprocessing the data (step 100). The patient-specific anatomical data may be obtained noninvasively, e.g., by CCTA.

A three-dimensional model of the patient's anatomy may be created based on the obtained anatomical data (step 200). For example, the three-dimensional model may be the three-dimensional model 10 of the patient's anatomy described above in connection with FIG. 1.

The three-dimensional model may be prepared for analysis and boundary conditions may be determined (step 300). For example, the three-dimensional model 10 of the patient's anatomy described above in connection with FIG. 1 may be trimmed and discretized into a volumetric mesh, e.g., a finite element or finite volume mesh. The volumetric mesh may be used to generate the equations 30 described above in connection with FIG. 1.

Boundary conditions may also be assigned and incorporated into the equations 30 described above in connection with FIG. 1. The boundary conditions provide information about the three-dimensional model 10 at its boundaries, e.g., inflow boundaries, outflow boundaries, vessel wall boundaries, etc. The inflow boundaries may include the boundaries through which flow is directed into the anatomy of the three-dimensional model, such as at an end of the aorta near the aortic root. Each inflow boundary may be assigned, e.g., with a prescribed value or field for velocity, flow rate, pressure, or other characteristic, by coupling a heart model and/or a lumped parameter model to the boundary, etc. The outflow boundaries may include the boundaries through which flow is directed outward from the anatomy of the three-dimensional model, such as at an end of the aorta near the aortic arch, and the downstream ends of the main coronary arteries and the branches that extend therefrom. Each outflow boundary can be assigned, e.g., by coupling a lumped parameter or distributed (e.g., a one-dimensional wave propagation) model. The prescribed values for the inflow and/or outflow boundary conditions may be determined by noninvasively measuring physiologic characteristics of the patient, such as, but not limited to, cardiac output (the volume of blood flow from the heart), blood pressure, myocardial mass, etc. The vessel wall boundaries may include the physical boundaries of the aorta, the main coronary arteries, and/or other coronary arteries or vessels of the three-dimensional model 10.

The computational analysis may be performed using the prepared three-dimensional model and the determined boundary conditions (step 400) to determine blood flow information for the patient. For example, the computational analysis may be performed with the equations 30 and using the computer 40 described above in connection with FIG. 1 to produce the images described above in connection with FIG. 1, such as the simulated blood pressure model 50, the simulated blood flow model 52, and/or the cFFR model 54.

The method may also include providing patient-specific treatment options using the results (step 500). For example, the three-dimensional model 10 created in step 200 and/or the boundary conditions assigned in step 300 may be adjusted to model one or more treatments, e.g., placing a coronary stent in one of the coronary arteries represented in the three-dimensional model 10 or other treatment options. Then, the computational analysis may be performed as described above in step 400 in order to produce new images, such as updated versions of the blood pressure model 50, the blood flow model 52, and/or the cFFR model 54. These new images may be used to determine a change in blood flow velocity and pressure if the treatment option(s) are adopted.

The systems and methods disclosed herein may be incorporated into a software tool accessed by physicians to provide a noninvasive means to quantify blood flow in the coronary arteries and to assess the functional significance of coronary artery disease. In addition, physicians may use the software tool to predict the effect of medical, interventional, and/or surgical treatments on coronary artery blood flow. The software tool may prevent, diagnose, manage, and/or treat disease in other portions of the cardiovascular system including arteries of the neck (e.g., carotid arteries), arteries in the head (e.g., cerebral arteries), arteries in the thorax, arteries in the abdomen (e.g., the abdominal aorta and its branches), arteries in the arms, or arteries in the legs (e.g., the femoral and popliteal arteries). The software tool may be interactive to enable physicians to develop optimal personalized therapies for patients.

For example, the software tool may be incorporated at least partially into a computer system, e.g., the computer 40 shown in FIG. 1 used by a physician or other user. The computer system may receive data obtained noninvasively from the patient (e.g., data used to create the three-dimensional model 10, data used to apply boundary conditions or perform the computational analysis, etc.). For example, the data may be input by the physician or may be received from another source capable of accessing and providing such data, such as a radiology or other medical lab. The data may be transmitted via a network or other system for communicating the data, or directly into the computer system. The software tool may use the data to produce and display the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Thus, the software tool may perform steps 100-500. In step 500, the physician may provide further inputs to the computer system to select possible treatment options, and the computer system may display to the physician new simulations based on the selected possible treatment options. Further, each of steps 100-500 shown in FIG. 2 may be performed using separate software packages or modules.

Alternatively, the software tool may be provided as part of a web-based service or other service, e.g., a service provided by an entity that is separate from the physician. The service provider may, for example, operate the web-based service and may provide a web portal or other web-based application (e.g., run on a server or other computer system operated by the service provider) that is accessible to physicians or other users via a network or other methods of communicating data between computer systems. For example, the data obtained noninvasively from the patient may be provided to the service provider, and the service provider may use the data to produce the three-dimensional model 10 or other models/meshes and/or any simulations or other results determined by solving the equations 30 described above in connection with FIG. 1, such as the simulated blood pressure model 50, the simulated blood flow model 52, and/or the cFFR model 54. Then, the web-based service may transmit information relating to the three-dimensional model 10 or other models/meshes and/or the simulations so that the three-dimensional model 10 and/or the simulations may be displayed to the physician on the physician's computer system. Thus, the web-based service may perform steps 100-500 and any other steps described below for providing patient-specific information. In step 500, the physician may provide further inputs, e.g., to select possible treatment options or make other adjustments to the computational analysis, and the inputs may be transmitted to the computer system operated by the service provider (e.g., via the web portal). The web-based service may produce new simulations or other results based on the selected possible treatment options, and may communicate information relating to the new simulations back to the physician so that the new simulations may be displayed to the physician.

As described above, the above described techniques for computational modeling for noninvasively calculating FFR may assume that: (i) the geometry is known with certainty, (ii) clinical variables such as blood pressure, hematocrit, myocardial mass, etc. are known with certainty, and/or (iii) boundary conditions at the inlet and outlets of the computational model are known with certainty. However, in reality, the FFR predicted using CFD varies based on the accuracy of the available data and mathematical models that describe hemodynamics in the arteries.

Accordingly, the present disclosure also describes methods and systems for incorporating and quantifying the effects of uncertainties in the available data, as well as mathematical models. In addition, the present disclosure describes methods and systems for assigning confidence intervals to determine FFR values, as well as rank the sensitivity of FFR calculations to different parameters.

Figure 3:
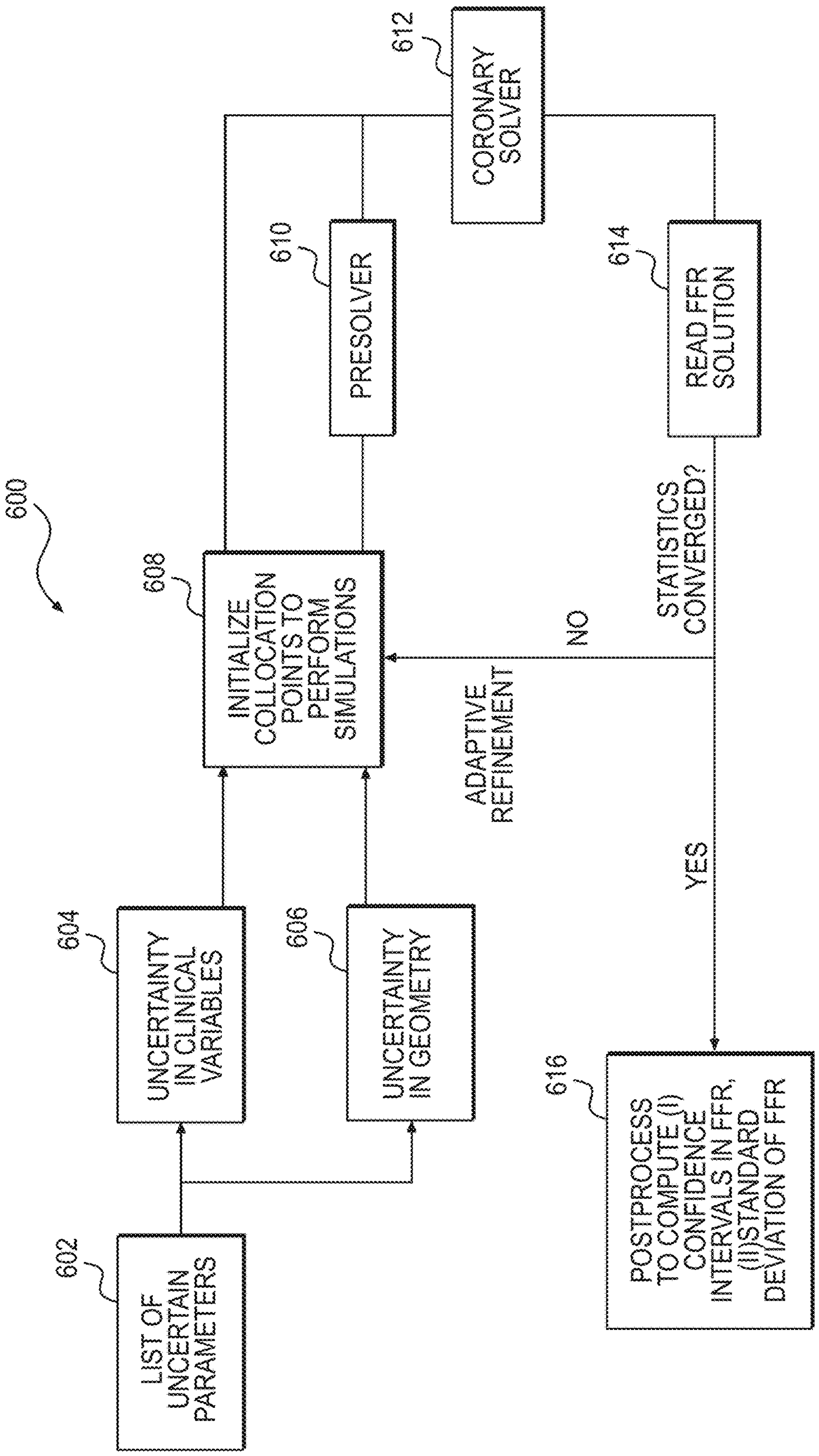
FIG. 3 is a flow chart that describes an exemplary process for defining input uncertainties, calculating analysis sensitivities, and calculating confidence intervals in FFR, according to an exemplary embodiment.

For example, FIG. 3 is a flow chart that describes an exemplary method 600 for defining input uncertainties, calculating FFR analysis sensitivities, and calculating confidence intervals in FFR, according to an exemplary embodiment. As shown in FIG. 3, method 600 may include a plurality of pre-processing steps, including defining sources of uncertainty and their magnitude. For example, method 600 may include generating a list of uncertain parameters (step 602), determining uncertainty in clinical variables (step 604), such as myocardial mass, hematocrit/viscosity, pressure, body/surface area, and/or geometric variables such as maximal stenosis diameter, stenosis length, etc., and determining uncertainty in patient geometry (step 606).

Method 600 may also include assigning a probability and/or error associated with each of the variables. By way of example, hematocrit may have a uniform distribution between 40 and 50 (any value between 40 and 50 is equally probable), blood pressure may be a Gaussian distribution with mean 100 mm Hg and standard deviation 10 mm Hg (the probabilities to pressure around 100 mm Hg may be assigned based on the Gaussian distribution). A stochastic space may therefore be defined as the range of these values. Although the present disclosure describes computing sensitivities using a stochastic collocation method, any other equivalent statistical technique for evaluating input sensitivities may be used. Moreover, although the present disclosure describes a stochastic collocation method based on the Smolyak quadrature method, again, any other equivalent method to compute sensitivities may be used. The Smolyak quadrature method is an exemplary method for interpolating and integrating functions when the number of input variables is higher than, e.g., 3 or 4. The stochastic collocation method may apply the Smolyak quadrature method to evaluate sensitivities and quantify the effect of input uncertainties on the outputs.

Method 600 may then include simulation and analysis steps for computing the effect of input uncertainty on outputs (step 608). For example, method 600 may include initializing collocation points, each of which corresponds to a unique combination of parameters, e.g., using a coarse sparse grid (depending on the number of parameters, n, the number of initial collocation points would be of the order of 2n or so). In one embodiment, the presently disclosed adaptive stochastic collocation method may split the created stochastic space into frozen and active patches (based on how the quantity-of-interest varies in the parameter space), and only the active patches may be further refined. Moreover, in one embodiment, adaptive refinement criterion may be chosen based on a difference in FFR between two successive grids. In addition, the solution at each collocation point may be initialized based on the solution obtained at the previous collocation point. Finally, the input uncertainties may be tailored to various blood flow and/or cardiac parameters, such as myocardial mass, viscosity, brachial pressure, etc.

For each of a plurality of collocation points, method 600 may optionally include performing various "pre-solving" techniques (step 610). For example, method 600 may include performing any of the various presolving techniques described in U.S. application Ser. No. 13/625,628, filed Sep. 24, 2012, the entirety of which is incorporated herein by reference.

Method 600 may then include, for each of a plurality of collocation points, executing a coronary solver (step 612) for performing simulations to non-invasively, and computationally, obtain one or more FFR values. For example, method 600 may include performing any of the various computational FFR modeling techniques described in U.S. Pat. No. 8,315,812, filed Jan. 25, 2011, the entirety of which is incorporated herein by reference. Thus, as described in the '812 patent, FFR values may be obtained by generating a flow approximation or surrogate computational model based on an anatomic model of a patient, and analyzing the surrogate computational model to estimate an FFR value for one or more locations in a patient's vasculature. For example, an anatomic model may be created by generating a three-dimensional anatomic model of a patient's coronary vasculature. A surrogate computation model or flow approximation of the anatomic model may then be created, e.g., by generating a reduced-order model of the patient's vasculature. In one embodiment, the reduced-order model may be a one-dimensional or lumped parameter model of the patient's vasculature. In one embodiment, the anatomic model may be a one-dimensional wave propagation model and the surrogate computational model may also be a one-dimensional wave propagation model.

In one embodiment, FFR values may be obtained using machine learning estimates as opposed to physics-based simulations. In other words, instead of executing a coronary solver, such as in the '812 patent, for each of the plurality of collocation points, method 600 may efficiently estimate blood flow characteristics based on knowledge gleaned from analyzing blood flow of numerous other patients. For example, method 600 may include performing any of the various machine learning techniques described in U.S. Provisional Patent Application No. 61/700,213, filed Sep. 12, 2012, the entirety of which is incorporated herein by reference. Thus, in one embodiment, FFR values may be obtained by training a machine learning algorithm to estimate FFR values for various points of patient geometry based on feature vectors of patient physiological parameters and measured blood flow characteristics, and then applying the machine learning algorithm to a specific patient's geometry and physiological parameters to obtain predicted FFR values.

Based on these results, method 600 may construct an approximation to FFR in the stochastic space. In one embodiment, method 600 may include reading the FFR solution(s) (step 614) and, for example, computing various means, standard deviations, and confidence intervals based on the reconstructed FFR.

Method 600 may then include determining whether "statistics converged" based on whether termination criteria were met, in which case method 600 may proceed to post processing steps (step 616), or they were not met, in which case method 600 may perform adaptive refinement and return to initializing collocation points for performing simulations (step 608). In one embodiment, termination criterion may determine whether the algorithm terminates based on whether all collocation points belong to a frozen set. A collocation point may be considered frozen if either (a) all of its neighbors are frozen, or (b) the FFR value at this collocation point between two consecutive refinement levels is less than a cut-off.

If termination criterion were met (i.e., statistics converged), then method 600 may include performing post-processing steps, such as evaluating statistics of the outputted FFR values (step 616). For example, using the reconstructed FFR, method 600 may evaluate a probability density function of the FFR at each spatial point (surface nodes). From this, the standard deviation of FFR and confidence intervals can be evaluated throughout the computational model.

One or more confidence interval values may be generated for each predicted FFR value, based on probability information generated in step 616. For example, the method may involve generating a confidence value for a specific generated FFR value (e.g., 90% confidence in an FFR value of 0.85). In one embodiment, the method may include re-calculating or re-estimating an FFR value if the determined confidence level is below a predetermined threshold (e.g., 90%). By outputting and displaying a confidence level in relation to each estimated FFR value, physicians may be provided with more information, insights, and certainty regarding the reliability of an estimated FFR value. For example, if a patient exhibits a problematic FFR value (e.g., less than 0.80) and the generated confidence level is high, a physician may be more confident in prescribing a treatment or intervention. By contrast, if a patient's FFR value is borderline problematic (e.g., 0.80 to 0.85) and the generated confidence level is low, a physician may be more inclined to perform further testing before prescribing a treatment or intervention.

As an alternative or additional embodiment, the method may include generating a range of FFR values consistent with a desired confidence interval. For example, given a desired confidence interval of 95%, the method may include generating a range of FFR values for which there is a 95% chance that the actual FFR value falls within the output range (e.g., there is a 95% confidence that FFR is 0.82-0.87). It will be appreciated that reducing the desired confidence value may cause narrowing of the outputted FFR range, whereas increasing the desired confidence value may cause expanding of the outputted FFR range. In one embodiment, any indication of a calculated sensitivity or confidence level may be displayed in relation to an output FFR value.

The exemplary method 600 of FIG. 3 may be performed by computer 40 of FIG. 1, or by any other computer(s), server(s), or handheld electronic device(s). Additional exemplary embodiments of method 600 will now be described with respect to both general and specific embodiments, any of which may be performed in combination with any of the techniques of U.S. application Ser. No. 13/625,628, filed Sep. 24, 2012, and/or of U.S. Pat. No. 8,315,812, filed Jan. 25, 2011. Accordingly, the above method 600 and the below described general and specific exemplary embodiments may be used to determine sensitivity of computed FFR values to input uncertainties, and/or calculate confidence intervals of computed FFR values based on determined sensitivity.

Exemplary Embodiment

In an exemplary general embodiment, a method for quantifying uncertainties in FFR calculations involves acquiring a digital representation of a CCTA scan of the patient, including all the arteries of interest. This scan may be stored and converted to a computational model of the patient-specific geometry of all the relevant blood vessels. The computational model may be trimmed at locations (determined by geometrical parameters) where specific boundary conditions are enforced, thus quantifying the effect of all vessels and micro-vessels downstream of that location. Values of clinical variables such as patient hematocrit, brachial blood pressure, etc. may be obtained.

In addition, uncertain parameters/variables may be identified and assigned, such as by identifying inputs that are uncertain, such as clinical variables, e.g., hematocrit, pressure, body surface area, and/or geometric variables, such as lesion size, lesion length, etc. A probability/error may be assigned and associated with each of the variables. The probability may model a combination of diurnal variation in the entity, noise in the data, inadequate information, and/or error incurred in using generalized empirical models. The method may involve analyzing which variables affect the quantity(ies) of interest, and choosing an optimal subset of the variables that might affect the quantities of interest.

The exemplary general method for quantifying uncertainties may also include certain pre-processing steps, such as constructing a coarse stochastic space for all identified variables. The method may include initializing stochastic collocation (e.g., quadrature) points using, for example, the Smolyak sparse grid algorithm, with each point corresponding to a unique combination of parameters. The number of collocation points may depend on the collocation (quadrature) level. Collocation levels may be nested, with level 0 corresponding to only one simulation and the number increasing with levels. The actual number may depend on the number of stochastic variables.

In one embodiment, if the technique identifies, e.g., n variables, then initially the collocation points may correspond to the quadrature points of a coarse (e.g., level 1) Smolyak sparse grid. These collocation points lie in a [0,1] hypercube space. The collocation points may be mapped from [0,1] to clinically relevant values using transformations employing the inverse cumulative distribution function. Then, each collocation point may correspond to a unique set of inputs to the simulations, and each collocation point may be assigned a status, i.e., “active” or “frozen.” In one embodiment, all collocation points may be initially assigned “active.”

The exemplary general method for quantifying uncertainties may then include performing CFD simulations at one or more of the collocation points. For example, in one embodiment, a CFD simulation may be performed at each identified point. If at least one active collocation point exists, the quadrature level may be incremented and only collocation points with at least one active neighbor may be picked. The quadrature level may be incremented, and for each new collocation point, the method may calculate the difference between a quantity of interest's interpolated value (e.g., using Lagrange polynomials) using the previous quadrature level and its actual value using a simulation. If this difference is less than a preset threshold, this collocation point may be labeled “frozen.” Otherwise, the point may be labeled “active.”

Finally, the exemplary general method for quantifying uncertainties may include certain post-processing steps, such as calculating variability in quantities of interest. For example, the method may include constructing Lagrange polynomial interpolates of a quantity of interest in the stochastic space, such as for predicting a quantity of interest corresponding to parameter combinations where simulations were not performed. In addition, the method may include computing a probability distribution function of the quantity of interest by sampling the stochastic space according to the assigned probabilities.

Exemplary Embodiment

Described below is a specific embodiment of the technique to quantify the effect of uncertainties and compute confidence intervals in the output.

1. Acquire a digital representation of the following information for a patient suspected to have coronary disease.
    a. A CCTA of the patient may be performed to visualize and compute all the vessels of interest, including ascending aorta, left/right coronary artery, left circumflex artery, left obtuse marginal, and/or all other vessels of interest that are visible. The scanned images may be cleaned and post-processed to obtain a computational domain within which simulations will be performed.
    b. In addition to CCTA, a set of clinical parameters may be measured, including heart-rate, systolic and diastolic brachial blood pressures, hematocrit, patient height and weight, and patient history, such as smoking status, presence/absence of diabetes, etc.
    c. A set of derived quantities may be calculated from steps (a) and (b). These derived quantities may include:
        i. Myocardial mass ($m_{myo}$)—Obtained by image segmentation of the left ventricle to calculate the volume of myocardium and multiplying it with a density (usually assumed constant ~1.05 g/cm^3).
        ii. Body surface area—Calculated from the patient height (h) and weight (w) as $$BSA = \sqrt{\frac{hw}{3600}}$$

iii. Viscosity—calculated from the hematocrit (hem) as $$\eta = \frac{c}{\left(1 - \frac{hem}{100}\right)^{2.5}}$$

where c is 0.0012.

iv. Inlet aortic flow rate (Q)—Calculated from scaling studies as $$Q = \frac{1}{60} BSA^{1.15}$$

v. Coronary flow rate ($q_{cor}$)—Calculated from myocardial mass as $$q_{cor} = c_{dil} \frac{5.09}{60} m_{myo}^{0.75}$$

where $c_{dil}$ is the dilation factor.

vi. Coronary resistance—The net coronary resistance is calculated from the desired coronary flow, and the value for individual outlets is calculated based on their areas.

vii. Resistance of outlet aorta—This may be calculated based on aortic pressure, aortic flow rate and desired coronary flow rate.

2. For each patient that underwent CCTA, identify and model the input uncertainties in the following exemplary manner:
   a. Clinical variables: Clinical parameters, especially those derived (1c), may be uncertain. They may be modeled using a probability distribution function, typically Gaussian, unless the exact form is known.
   b. Geometry variables: Size of vessel wall (especially near lesions), length of lesions and location of trim planes.
   c. Modeling assumptions: Coronary flow rate versus mass (dependence on other parameters), aortic flow rate on BSA, outflow resistances on the area of trimmed outlets.
3. Construct a coarse stochastic space of all uncertain entities:
   a. Each combination of parameters may correspond to a quadrature or collocation point. For one dimension, the collocation points may correspond to Chebyshev nodes (zeros of the Chebyshev polynomials) in the interval 0 to 1. These can be extended to multiple dimensions by constructing a tensor product of the one-dimensional Chebyshev nodes. The Smolyak sparse grid may choose a subset of these nodes to accelerate convergence but still maintaining accuracy.
   b. For a given variable, say $\alpha$, the transformation from $\xi \in [0,1]$ to $[\alpha_L, a_U]$ may follow the inverse cumulative distribution function (cdf) of $\alpha$, $\alpha=\mu_\alpha+\sigma_\alpha cdf^{-1}(2\xi-1)$ where $\mu_\alpha$ is the mean value of $\alpha$ and $\sigma_\alpha$ is its standard deviation. To prevent unbounded transformations for pdf's with infinite support (e.g., Gaussian distribution), $\xi$ may be initially mapped to [0.01, 0.99] prior to the inverse CFD transformation in such cases. If $\alpha$ is a Gaussian variable, this may transform to $\alpha=\mu_\alpha+erf^{-1}(0.99*(2\xi-1))$. Each abscissa of the collocation point may be transformed based on this function.
   c. The following variables may be assumed Gaussian with a mean and standard deviation. Standard deviations for blood pressure, myo-mass scaling coefficient, and viscosity may be derived from literature studies. Standard deviation for the myocardial mass may be obtained from an in-house gage study (density may be assumed constant).

| variable | mean | coefficient of variation |
|---|---|---|
| viscosity | $\eta = \frac{c}{\left(1 - \frac{hem}{100}\right)^{25}}$ | 10% |
| blood pressure | $(P_{sys} + 2\ P_{dias})/3$ | 10% |
| myocardial mass | myocardium segmentation | 7.5% |
| coefficient | 0.083 | 15% |

d. For calculating sensitivity due to geometry, each segment of vessel between two ostia points may be assumed to be represented using a single random variable, which dilates or contracts the segment. If there are multiple stenoses in serial, correlated random variables may also be used to model uncertainty in geometry. The amount of vaso-dilation or vaso-contraction may be determined on a lesion-specific basis. Other techniques for dilating and contracting, such as using the radius along the centerline, 3D position of each node, and/or grouping together nodes between ostia, may also be used.
   e. Each grouping of the vessel may be further analyzed. For instance, if the sensitivity of a group is deemed high, it may be split into two groups, and procedure (e) is repeated until sufficient localization of high sensitivity regions is achieved.
4. Processing:
   a. At each active collocation point, CFD simulations may be performed using resistance boundary conditions (the ratio of pressure drop to flow rate is a constant). The pressure and velocity solutions at each collocation point may be initialized based on the solution obtained at the previous collocation point. Lumen locations where the pressure drop in the model is the highest may be chosen as candidate locations to determine termination criterion of the collocation algorithm. Based on these results, an approximation to FFR in the stochastic space may be constructed.
   b. The collocation level may be incremented. At the new collocation points, the difference in the FFR at the ten identified locations between simulation and interpolated value using the previous collocation level may be calculated. A tolerance of $10^{-2}$ may be set, and hence the status of a point may be changed to frozen if if $|FFR_{sim}-FFR_{interp}|<=10^{-2}$. This step may be repeated until all collocation points are frozen.
5. Post-processing:
   a. Mean, standard deviation, and lower order moments of FFR may be obtained by integrating the FFR at each spatial location in the stochastic space. This may be performed by integrating products of Lagrange polynomials (offline) and summing the result with corresponding FFR solution obtained through the solution.
   b. Confidence intervals may be calculated by sampling the stochastic space at between 50000-100000 points, extracting a histogram, and subsequently extracting the cumulative distribution function.

One or more of the steps described herein may be performed by one or more human operators (e.g., a cardiologist or other physician, the patient, an employee of the service provider providing the web-based service or other service provided by a third party, other user, etc.), or one or more computer systems used by such human operator(s), such as a desktop or portable computer, a workstation, a server, a personal digital assistant, etc. The computer system(s) may be connected via a network or other method of communicating data.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

Various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for decision support for therapy, the method comprising:

segmenting organ data representing an organ of a first patient from a plurality of scan data from a medical scanner, the plurality of scan data representing a volume of the first patient, wherein the segmented organ data comprises data regarding a coronary vasculature of the first patient, wherein the segmenting is image-based segmentation;

simulating, by a processor, an initial organ-specific physiological model wherein the initial organ-specific physiological model is generated from the segmented organ data and a first treatment of a plurality of different treatments, wherein the plurality of different treatments includes medication-only treatments, interventional treatments, and/or surgical treatments;

estimating, by the processor, one or more initial uncertainties in the initial organ-specific physiological model;

generating, by a processor, for each of the one or more initial uncertainties, one or more initial blood flow characteristic values;

determining, by a processor, at least one statistical variation of the blood flow characteristic values for each of the one or more initial uncertainties;

simulating, by a processor, a new organ-specific physiological model using a second treatment of the plurality of treatments, wherein the first treatment and the second treatment are different treatments;

estimating, by the processor, one or more new uncertainties in the new organ-specific physiological model;

generating, by a processor, for each of the one or more new uncertainties, one or more new blood flow characteristic values; and providing for display, by a processor, (1) the initial organ-specific physiological model or (2) the new organ-specific physiological model, wherein the initial and new organ-specific physiological models each are a three-dimensional anatomic model of coronary vasculature of the first patient.

2. The method of claim 1 wherein simulating comprises identifying past patients similar to the first patient and using past patient blood flow characteristics for the different treatments as a simulation for the first patient.

3. The method of claim 1, wherein estimating the one or more initial uncertainties comprises estimating the one or more initial uncertainties based on variability of the initial organ-specific physiological model.

4. The method of claim 1, wherein providing comprises presenting the organ-specific physiological models and respective estimated uncertainties in a ranked order.

5. The method of claim 1 wherein segmenting the organ data comprises segmenting the organ data representing at least one coronary artery.

6. A system for decision support for therapy for a patient, the system comprising:

a data storage device that stores instructions for processing images to determine blood flow information; and a processor configured to execute the instructions to perform operations comprising:

segmenting organ data representing an organ of a first patient from a plurality of scan data from a medical scanner, the plurality of scan data representing a volume of the first patient, wherein the segmented organ data comprises data regarding a coronary vasculature of the first patient, wherein the segmenting is image-based segmentation;

simulating, by a processor, an initial organ-specific physiological model wherein the initial organ-specific physiological model is generated from the segmented organ data and a first treatment of a plurality of different treatments, wherein the plurality of different treatments includes medication-only treatments, interventional treatments, and/or surgical treatments;

estimating, by the processor, one or more initial uncertainties in the initial organ-specific physiological model;

generating, by a processor, for each of the one or more initial uncertainties, one or more initial blood flow characteristic values;

determining, by a processor, at least one statistical variation of the blood flow characteristic values for each of the one or more initial uncertainties;

simulating, by a processor, a new organ-specific physiological model using a second treatment of the plurality of treatments, wherein the first treatment and the second treatment are different treatments;

estimating, by the processor, one or more new uncertainties in the new organ-specific physiological model;

generating, by a processor, for each of the one or more new uncertainties, one or more new blood flow characteristic values; and providing for display, by a processor, (1) the initial organ-specific physiological model or (2) the new organ-specific physiological model, wherein the initial and new organ-specific physiological models each are a three-dimensional anatomic model of coronary vasculature of the first patient.

7. The system of claim 6, wherein simulating comprises identifying past patients similar to the first patient and using past patient blood flow characteristics for the different treatments as a simulation for the first patient.

8. The system of claim 6, wherein estimating the one or more initial uncertainties comprises estimating the one or more initial uncertainties based on variability of the initial organ-specific physiological model.

9. The system of claim 6, wherein providing comprises presenting the organ-specific physiological models and respective estimated uncertainties in a ranked order.

10. The system of claim 6, wherein segmenting the organ data comprises segmenting the organ data representing a vessel.

11. A non-transitory computer-readable medium for use on at least one computer system containing computer executable programming instructions for decision support for therapy, the instructions comprising steps for:

segmenting organ data representing an organ of a first patient from a plurality of scan data from a medical scanner, the plurality of scan data representing a volume of the first patient, wherein the segmented organ data comprises data regarding a coronary vasculature of the first patient, wherein the segmenting is image-based segmentation;

simulating, by a processor, an initial organ-specific physiological model wherein the initial organ-specific physiological model is generated from the segmented organ data and a first treatment of a plurality of different treatments, wherein the plurality of different treatments includes medication-only treatments, interventional treatments, and/or surgical treatments;

estimating, by the processor, one or more initial uncertainties in the initial organ-specific physiological model;

generating, by a processor, for each of the one or more initial uncertainties, one or more initial blood flow characteristic values;

determining, by a processor, at least one statistical variation of the blood flow characteristic values for each of the one or more initial uncertainties;

simulating, by a processor, a new organ-specific physiological model using a second treatment of the plurality of treatments, wherein the first treatment and the second treatment are different treatments;

estimating, by the processor, one or more new uncertainties in the new organ-specific physiological model;

generating, by a processor, for each of the one or more new uncertainties, one or more new blood flow characteristic values; and providing for display, by a processor, (1) the initial organ-specific physiological model or (2) the new organ-specific physiological model, wherein the initial and new organ-specific physiological models each are a three-dimensional anatomic model of coronary vasculature of the first patient.

12. The non-transitory computer-readable medium of claim 11, wherein simulating comprises identifying past patients similar to the first patient and using past patient blood flow characteristics for the different treatments as a simulation for the first patient.

13. The non-transitory computer-readable medium of claim 11, wherein estimating the one or more initial uncertainties comprises estimating the one or more initial uncertainties based on variability of the initial organ-specific physiological model.

14. The non-transitory computer-readable medium of claim 11, wherein providing comprises presenting the organ-specific physiological models and respective estimated uncertainties in a ranked order.

15. The non-transitory computer-readable medium of claim 11, wherein segmenting the organ data comprises segmenting the organ data representing at least one coronary artery.

* * * * *